(12) United States Patent
Rudser

(10) Patent No.: US 10,117,664 B2
(45) Date of Patent: Nov. 6, 2018

(54) COMBINED TUNNELING TOOLS

(71) Applicant: HeartWare, Inc., Miami Lakes, FL (US)

(72) Inventor: John Rudser, Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 282 days.

(21) Appl. No.: 15/041,257

(22) Filed: Feb. 11, 2016

(65) Prior Publication Data

US 2016/0235427 A1    Aug. 18, 2016

Related U.S. Application Data

(60) Provisional application No. 62/115,998, filed on Feb. 13, 2015.

(51) Int. Cl.
| | | |
|---|---|---|
| *A61B 17/14* | (2006.01) | |
| *A61B 17/32* | (2006.01) | |
| *A61B 17/88* | (2006.01) | |
| *A61M 1/10* | (2006.01) | |
| A61B 17/34 | (2006.01) | |
| A61B 17/00 | (2006.01) | |
| A61B 90/00 | (2016.01) | |
| A61M 1/12 | (2006.01) | |

(52) U.S. Cl.
CPC ........ *A61B 17/32* (2013.01); *A61B 17/00234* (2013.01); *A61B 17/320016* (2013.01); *A61B 17/8875* (2013.01); *A61M 1/10* (2013.01); A61B 17/3415 (2013.01); A61B 2017/0046 (2013.01); A61B 2017/00353 (2013.01); A61B 2017/00464 (2013.01); A61B 2017/00477 (2013.01); A61B 2017/320056 (2013.01); A61B 2090/031 (2016.02); A61M 1/101 (2013.01); A61M 1/1008 (2014.02); A61M 1/122 (2014.02)

(58) Field of Classification Search
CPC .............. A61B 17/32; A61B 17/00234; A61B 17/8875; A61B 17/320016; A61B 2017/00477; A61B 2017/00353; A61B 2017/0046; A61B 17/3415; A61B 2017/00464; A61B 2090/031; A61M 1/10; A61M 1/1008; A61M 1/101; A61M 1/122; B25B 13/005; B25B 15/02; B25B 15/001; B25G 1/063; B25G 1/066
USPC ................................................ 81/177.5, 439
See application file for complete search history.

(56) References Cited

U.S. PATENT DOCUMENTS

| | | | | |
|---|---|---|---|---|
| 2,773,529 | A * | 12/1956 | Valenti .................. | B25B 13/481 81/177.7 |
| 3,186,265 | A * | 6/1965 | Wenturine ............ | B25B 13/463 81/177.9 |
| 3,272,246 | A * | 9/1966 | Bohnet .................. | B25B 15/02 81/28 |
| 3,908,637 | A | 9/1975 | Doroshow | |
| 4,236,266 | A * | 12/1980 | Hannah ................ | B25B 13/005 7/100 |

(Continued)

*Primary Examiner* — Amy R Weisberg
(74) *Attorney, Agent, or Firm* — Christopher & Weisberg, P.A.

(57) ABSTRACT

A surgical device includes a handle body extending along a handle axis. The handle body is releasably engaged to a tunneling shaft extending along a shaft axis transverse to the handle axis. At least one tool is mounted to the handle body. Each tool includes a working end adapted to actuate an element of an implantable device.

17 Claims, 10 Drawing Sheets

(56) References Cited

U.S. PATENT DOCUMENTS

| | | | | |
|---|---|---|---|---|
| 4,334,445 A * | 6/1982 | Timewell | | B25G 1/063 81/177.7 |
| 4,696,208 A * | 9/1987 | Lay | | B25B 13/462 81/58 |
| 5,053,043 A | 10/1991 | Gottesman et al. | | |
| 5,406,866 A * | 4/1995 | Badiali | | B25B 15/02 81/57.3 |
| 5,417,527 A * | 5/1995 | Wienhold | | B25B 15/001 279/75 |
| 5,450,775 A * | 9/1995 | Kozak | | B25B 15/02 81/177.4 |
| 5,665,093 A * | 9/1997 | Atkins | | A61B 17/3415 606/1 |
| 5,881,609 A * | 3/1999 | Palmer | | B25B 13/462 192/43 |
| 6,047,619 A * | 4/2000 | Anderson | | B25F 1/003 7/118 |
| 6,199,456 B1 * | 3/2001 | Hlady | | B25G 1/005 81/125.1 |
| 6,605,094 B1 | 8/2003 | Mann et al. | | |
| 6,669,708 B1 | 12/2003 | Nissenbaum et al. | | |
| 6,845,692 B2 * | 1/2005 | Cooper | | B25G 1/043 81/177.2 |
| 7,218,970 B2 | 5/2007 | Ley et al. | | |
| 7,270,669 B1 | 9/2007 | Sra | | |
| 7,335,216 B2 | 2/2008 | Bender et al. | | |
| 7,494,304 B2 * | 2/2009 | McAuliffe | | B23G 1/261 408/124 |
| 7,655,014 B2 | 2/2010 | Ko et al. | | |
| 7,938,045 B2 * | 5/2011 | Itoh | | B25B 15/02 81/177.4 |
| 8,065,938 B1 * | 11/2011 | Kravitch | | B25B 13/48 81/177.2 |
| 8,157,813 B2 | 4/2012 | Ko et al. | | |
| 8,333,686 B2 | 12/2012 | Marseille et al. | | |
| 8,409,233 B1 * | 4/2013 | Chinn | | A61B 17/3401 606/170 |
| RE44,675 E * | 12/2013 | Hawkins | | B25G 1/085 7/138 |
| 9,724,817 B2 * | 8/2017 | Hongquan | | B25G 1/066 |
| 2004/0064186 A1 * | 4/2004 | McCleary | | A61B 17/1659 623/18.11 |
| 2004/0147940 A1 | 7/2004 | Crawford | | |
| 2005/0283137 A1 * | 12/2005 | Doyle | | A61B 17/1222 606/1 |
| 2007/0173879 A1 * | 7/2007 | Pandey | | A61B 17/06109 606/190 |
| 2007/0276391 A1 * | 11/2007 | Graves | | A61B 17/1617 606/80 |
| 2008/0196559 A1 * | 8/2008 | Allan | | B25B 15/02 81/177.85 |
| 2009/0030444 A1 * | 1/2009 | Pandey | | A61B 17/32 606/190 |
| 2010/0160715 A1 * | 6/2010 | Deng | | A61B 17/3209 600/30 |
| 2010/0206099 A1 * | 8/2010 | Diao | | A61B 10/06 73/866.5 |
| 2010/0286670 A1 * | 11/2010 | Doyle | | A61B 17/1222 606/1 |
| 2012/0016377 A1 | 1/2012 | Geroy | | |
| 2012/0083818 A1 | 4/2012 | Pandey | | |
| 2013/0053856 A1 * | 2/2013 | Penenberg | | A61B 17/1659 606/91 |
| 2013/0118322 A1 * | 5/2013 | Seber | | B25B 15/00 81/440 |
| 2013/0178854 A1 * | 7/2013 | Sholev | | A61B 17/0469 606/79 |
| 2013/0304083 A1 * | 11/2013 | Kaercher | | A61B 17/00 606/130 |
| 2014/0316423 A1 * | 10/2014 | Schafer | | A61B 17/8875 606/104 |
| 2015/0313613 A1 * | 11/2015 | Rosse | | A61B 17/1631 606/81 |
| 2015/0367498 A1 * | 12/2015 | Chou | | B25B 13/461 81/60 |
| 2016/0107304 A1 * | 4/2016 | Hongquan | | B25B 15/04 81/177.8 |
| 2017/0156739 A1 * | 6/2017 | Nino | | A61B 17/1728 |

* cited by examiner

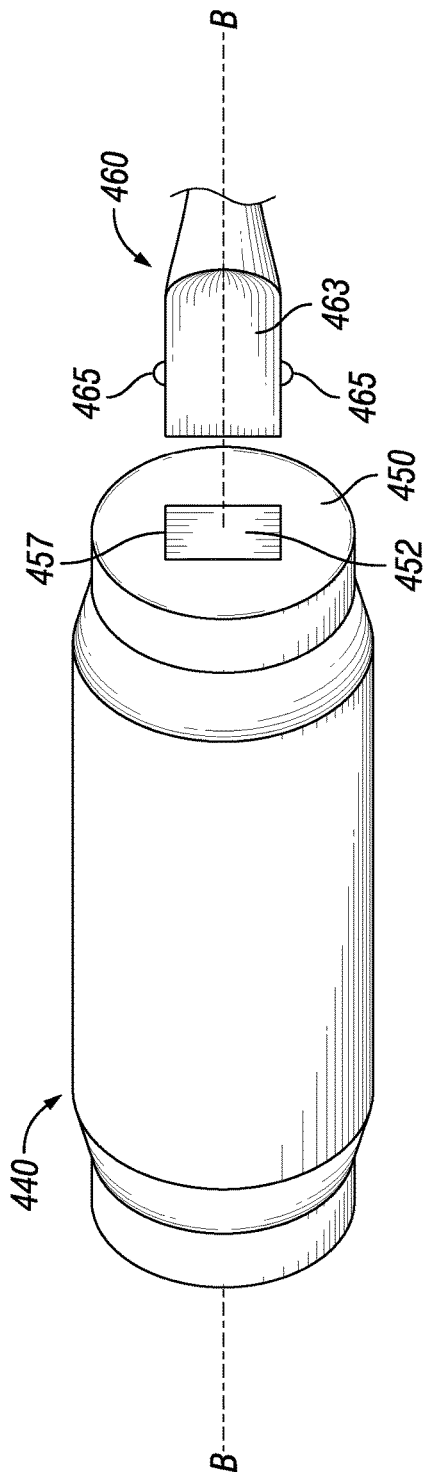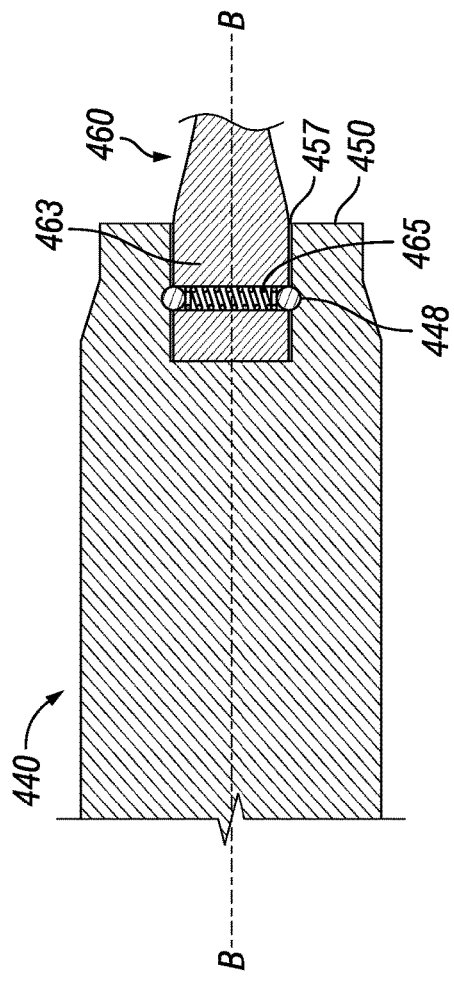
FIG. 6A
FIG. 6B

COMBINED TUNNELING TOOLS

CROSS-REFERENCE TO RELATED APPLICATION

This application claims the benefit of the filing date of U.S. Provisional Patent Application No. 62/115,998 filed Feb. 13, 2015, the disclosure of which is hereby incorporated by reference.

BACKGROUND OF THE INVENTION

The present invention relates to a combined tunneling tool for use with a medical device implanted within an animal; or, more particularly, for use with an implanted ventricular assist device (VAD) and system.

In certain disease states, the heart lacks sufficient pumping capacity to maintain adequate blood flow to the body's organs and tissues. For example, conditions such as ischemic heart disease and hypertension may leave the heart unable to fill and pump efficiently. This condition, also called congestive heart failure, may lead to serious health complications and even death. In fact, congestive heart failure is one of the major causes of death in the Western world.

This inadequacy of the heart can be alleviated by providing a mechanical pump also referred to as a ventricular assist device ("VAD") to supplement the pumping action of the heart. VADs may be used to assist the right ventricle, the left ventricle, or both. For example, a VAD may assist the left ventricle by mechanically pumping oxygenated blood from the left ventricle into the aorta. In this case, one or more pumps are implanted within the body of the patient to receive blood from the left ventricle and then push it into the aorta for distribution throughout the body. Such pumps may have an inflow opening and an outflow opening. In some cases, the inflow opening of a pump is positioned in the ventricle, while the outflow opening is connected to an outflow cannula extending to the aorta. In other cases, the inflow opening of a pump is connected to an inflow cannula connected to the ventricle.

U.S. Pat. Nos. 7,575,423, 7,976,271, 8,007,254, and 8,419,609, the disclosures of which are hereby incorporated by reference, disclose certain rotary blood pumps which can be used as ventricular assist devices. These pumps are usually powered by electricity. Typically, these pumps and other implantable components are hydraulically and electrically connected together through a plurality of implanted connections that supply electric power and blood to the pump. Each of these connections must continue to perform for extended periods of time, such as years or decades, without failure. Likewise, each internal connection must withstand movement of the surrounding body tissues and resist contamination by body fluids. For example, the implanted connections between the pump and an outflow or inflow cannula may be made by using a screwdriver to tighten a screw until an impermeable seal is formed.

A variety of internal connections may be employed within a VAD system. This has resulted in a corresponding variety of tools, each typically being specialized to actuate specific features of each connection. In some case, an operating surgeon may need to have ready access to as many as three or four different tools. For example, in many VAD implantation procedures, the surgeon must have access to at least a tunneling tool with a handle body, such as that described in U.S. Pat. No. 8,088,138 ("the '138 Patent") and U.S. Patent Publication Nos. 2009/0030444 and 2012/0083818, the disclosures of which are hereby incorporated by reference. Each of the tunneling tool and handle body are generally required to tunnel components of the VAD system through the body prior to making any internal connections. At present, neither of these tools is sufficient to complete a VAD implantation; thus, an additional set of tools is required to make the internal connections.

Unfortunately, having additional tools in the operating room creates numerous problems. Despite even the most stringent procedures, for example, these additional tools can be unintentionally left inside the body, especially if the tool is a relatively small, stand-alone item. This may require a second procedure to remove the implanted tool. Moreover, having a plurality of tools in the operating room also creates the possibility that a certain tool will become misplaced or contaminated in advance of or during the procedure. Further improvement would be desirable.

BRIEF SUMMARY OF THE INVENTION

In one aspect of the present invention, a surgical device includes a handle body extending along a handle axis. The handle body is releasably engaged to a tunneling shaft extending along a shaft axis transverse to the handle axis. At least one tool is mounted to the handle body. Each tool includes a working end adapted to actuate an element of an implantable device.

In another aspect of the present invention, a surgical method includes releasably securing a tunneling shaft to a handle body; moving the handle body and the tunneling shaft to create a tunnel within a living body and advance an elongate implantable element through the tunnel; removing the tunneling shaft from the handle body; and using a working end of the at least one tool mounted on the handle body to operate a feature of the implanted device.

In a further aspect of the present invention, a surgical kit includes at least one tunneling shaft extending along a shaft axis. In addition, the kit includes a handle body that extends along a handle axis. The handle body is engageable with each tunneling shaft so that the shaft axis is transverse to the handle axis. The kit also includes a plurality of tools, each of which are permanently mounted on the handle body or are adapted for temporary mounting on the handle body. Each tool includes a working end adapted to actuate an element of an implantable device.

BRIEF DESCRIPTION OF THE DRAWINGS

The features, aspects, and advantages of the invention will become better understood with regard to the following description, appended claims, and accompanying drawings in which:

FIG. 6A is a perspective view of a handle body and tool according to an even further embodiment of the present disclosure, the tool being in a first position.

FIG. 6B is a cross-sectional of the handle body and tool of FIG. 6A taken along a midline thereof, the tool being in a second position.

DETAILED DESCRIPTION

One aspect of the present invention is directed to devices, systems, methods, and kits for using a limited number of tools to create a pathway in the subcutaneous tissue of a body and connect various components implanted in the body.

Figure 1:
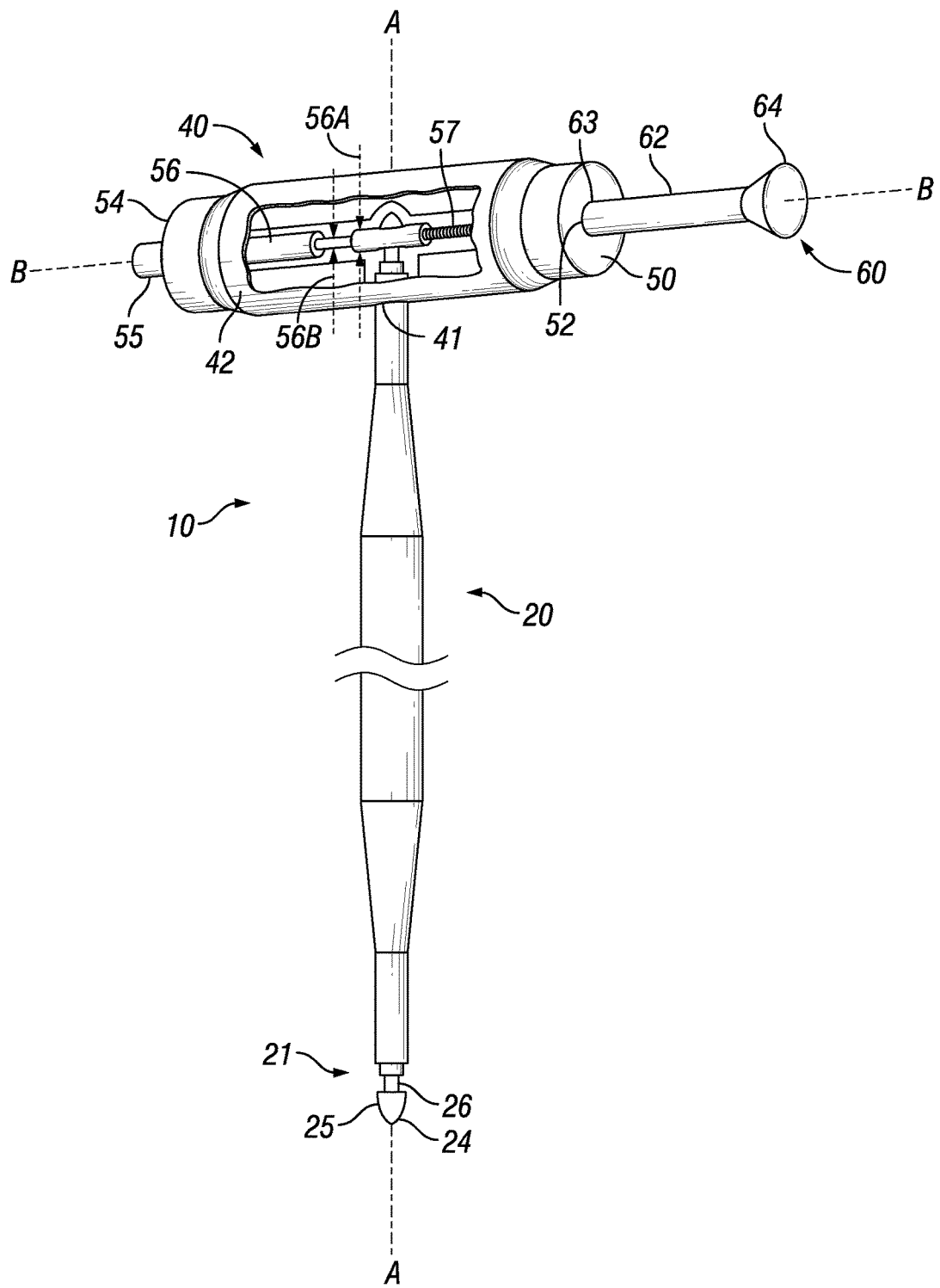
FIG. 1 is a partial cutaway perspective view of a device including a tunneling shaft, handle body and tool according to an embodiment of the present disclosure.

FIG. 1 depicts a device 10 having a tunneling shaft 20, a handle body 40, and at least one tool 60 mounted on a tooling end 50 of handle body 40. Handle body 40 preferably has an exterior surface 42 extending along a handle axis B-B between the tooling end 50 and an actuator end 54. Solely for purposes of illustration, the handle body is depicted in cutaway view to show internal components in FIG. 1; in practice. In FIG. 1, handle body 40 also has an opening 41 that extends into handle body 40 along a shaft axis A-A to receive at least one connection end 21 of tunneling shaft 20. Preferably, each end of tunneling shaft 20 has an identical connection end 21 that is interchangeably receivable within opening 41 on handle body 40. Each of these parts may be manufactured using biocompatible material, and may require one or more sterilization cycles between uses.

An exemplary embodiment of connection end 21 is depicted in FIG. 1 and described in the '138 Patent. As shown, each connection end 21 has a tip 24 defined by a tapered surface 25 and a groove 26. Connection end 21, and more specifically, a designated length of tip 24, is inserted into opening 41 to attach tunneling shaft 20 and handle body 40.

The actuator end 54 of the handle body has a first actuator 55 adapted to secure and release shaft 20 in or from opening 41. For example, as shown in the cut-away view provided by FIG. 1, first actuator 55 may have an engagement rod 56 with a diameter 56A sized for receipt within groove 26 of the tunneling tool and a diameter 56B that is smaller than diameter 56A. Preferably, actuator 55 is attached to at least one spring 57 housed within handle body 40 to bias first actuator 55 toward the unreleased position shown in FIG. 1. The first actuator 55 can be depressed to move rod 56 to a released position, in which the smaller second diameter 56B is aligned with opening 41 of the handle body. While the engagement rod is in this position, an end 21 of the tunneling tool is inserted into opening 41. Once the end of the tunneling tool is inserted, the first actuator is released and the engagement rod 56 moves back to the unreleased position, thus engaging the first diameter 56 in the groove 26 of the tunneling tool end so that the tip 24 cannot be pulled out of opening 41 in handle body 40. The actuator 55 can be depressed again to move the engagement rod back to the released position and allow withdrawal of the tunneling tool end from the handle. As a result, connection end 21 of tunneling shaft 20 is releasably secured to handle body 40.

Advantageously, this configuration permits handle body 40 to be utilized independently of shaft 20 to operate working end 64 of the at least one tool 60. For example, working end 64 may be adapted to actuate an element of an implantable device, such as tightening screw or clamping element, while handle body 40 is detached from shaft 20. The features of first actuator 55 and shaft 56 may be similar to those disclosed in the '138 Patent. When the tunneling shaft is engaged with the handle, the handle and tunneling shaft may be used generally as disclosed in the '138 Patent to form an elongated tunnel within soft tissues of the subject, and to pull an elongated element of an implantable device, such as an electrical power cable commonly referred to as a "driveline" though the tunnel. Likewise, the handle and tunneling shaft can be used to pull a flow conduit through the tunnel.

In FIG. 1, only one tool 60 is mounted to handle body 40, and the tool 60 is fixed in place on the handle body. Tool 60 has a connection end 63 opposite of working end 64. In FIG. 1, for example, connection end 63 of tool 60 is mounted to tooling end 50 of handle body 40 at a connection point 52. For example, tool 60 may be welded to tooling end 50. Although shown as being mounted coaxial with axis B-B, it should be appreciated that connection end 63 can be mounted at any connection point 52 on tooling end 50. A tool shaft 62 extends between connection end 63 and working end 64 of tool 60. Because of shaft 62, working end 64 may be disposed remotely from tooling end 50 to actuate an element of an implantable device within a body of a subject, such as a human patient undergoing surgery. For example, in FIG. 1, working end 64 is a closed wrench adapted to actuate a remote clamping feature of an implantable device by rotation of handle body 40 about axis B-B.

Several method steps for using shaft 20, handle body 40, and tool 60 are also disclosed in this application. A preferred surgical method comprises the step of mounting tunneling shaft 20 to handle body 40. Once mounted, and handle body 40 and shaft 20 are preferably moved to create a tunnel within a living body and advance at least a portion of an implantable element through the tunnel. Tunneling shaft 20 is then removed from the handle body 40 so that working end 64 of tool 60 may be used to actuate a feature of implanted device.

Numerous alternative embodiments of shaft 20, handle body 40, and tool 60 are also disclosed herein. Each alternate embodiment may have like elements that are labeled with like reference numbers, but within in alternate series of numbers, such as 100, 200, etc.

Figure 8:
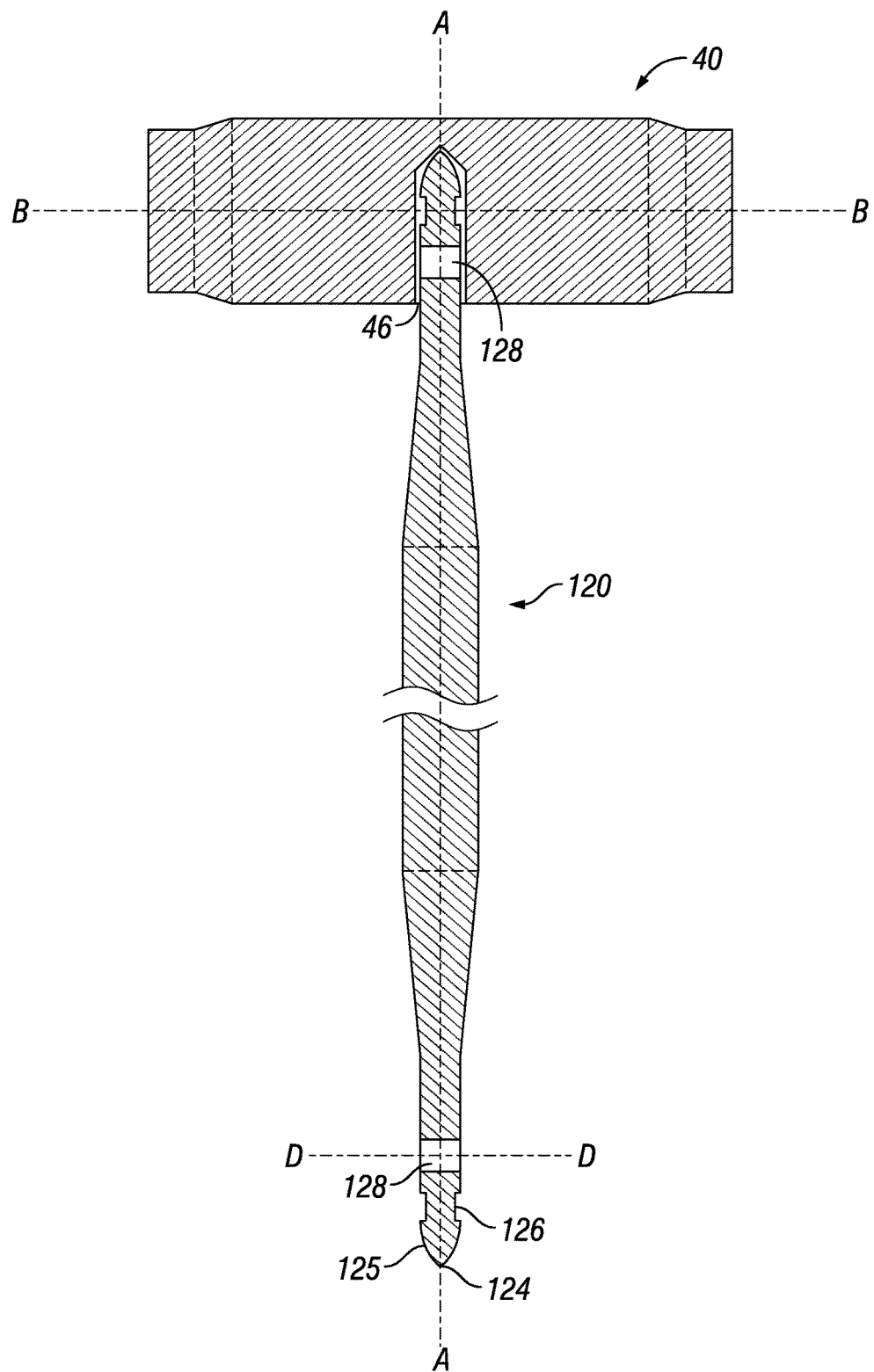
FIG. 8 is a schematic cross-sectional view of a tunneling shaft according to another embodiment of the present disclosure connected to a handle body.
Figure 9:
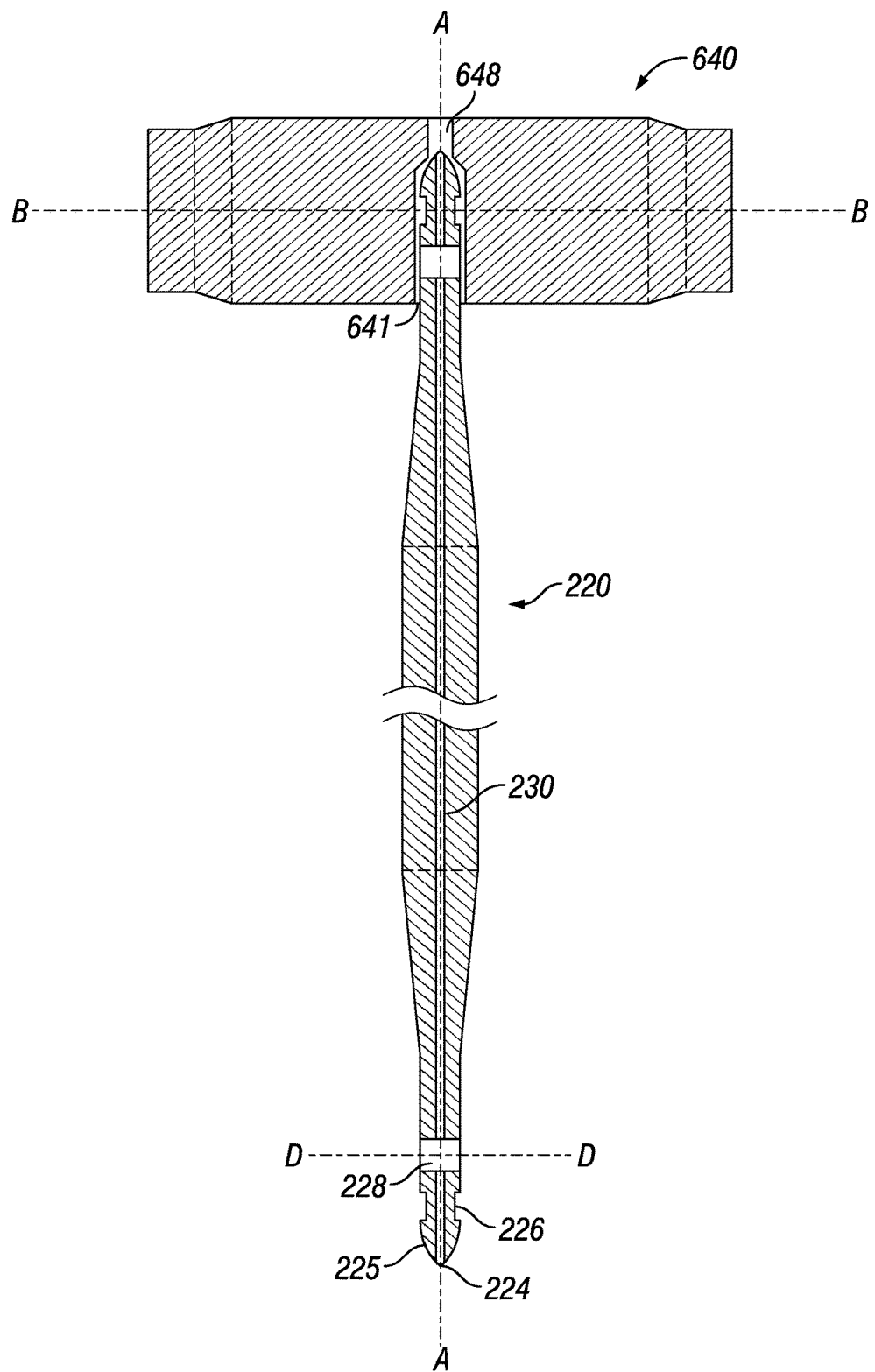
FIG. 9 is a schematic cross-sectional view of a tunneling shaft according to a further embodiment of the present disclosure connected to a handle body.

Alternate embodiments of tunneling shaft 20 are depicted in FIGS. 8 and 9 as tunneling shafts 120 or 220. Tunneling shaft 120 of FIG. 8, has a shaft hole 128 extending along a shaft hole axis D-D that is transverse to shaft axis A-A. Hole 128 may extend through any portion of shaft 120, such as a tip 124, tapered surface 125, or groove 126 and may be within opening 46 of handle 40. Hole 128 permits attachment of a catch element adapted to pull or push an elongated portion of the implantable device through the tunnel formed by shaft 120. For example, the catch element may be a thread or wire that can be affixed to shaft 20 by insertion through hole 128. Once attached, the thread or wire can be used to pull the elongated element of an implantable device, such as a driveline or conduit, through the tunnel. Shaft 20 and handle 40 may also be adapted to receive a guidewire therein. For example, as in FIG. 9, a shaft 220 has at least one hole 228 extending through a tip 224, tapered surface 225, or groove 226, the hole 228 in communication with a tunnel bore 230 extending through tunneling shaft 220 along shaft axis A-A. In complement, a handle body 640 has an opening 641 and a guidewire opening 648 that is coaxial with shaft axis A-A. Desirably, this configuration permits a guidewire to be inserted through tunnel bore 230 so that handle body 640 can be used to guide tunneling shaft 220 towards a targeted connection point. Bore 230 also allows an elongated portion of an implantable device, such as an electrical wire, to be advanced through the body as shaft 220 is moved through the body.

Numerous embodiments of the working end 64 of the tool (FIG. 1) also can be used in embodiments of the present invention. For example, working end 64 could also be selected from a group consisting of a closed or open wrench, hex driver, screwdriver, other specialized tool, and a combination thereof. Any portion of tool 60 may have a torque limiting element that ensures tightening of an element of the implantable device to a specified torque. For example, tool 60 may be a torque limiting screwdriver adapted to allow working end 64 to rotate about axis B-B relative to connection end 63 until the torque applied by working end 64 exceeds a predetermined maximum value. Alternatively, any embodiment of tool 60 may also have a ratcheting feature that allows working end 64 to be rotated about axis B-B in a first working direction, where working end 64 is fixed relative to connection end 63, and a second release direction, where working end 64 is moveable relative to connection end 63. Either the torque limiting or ratcheting feature may be adjustable to modify the pre-determined amount of torque applied by or rotational direction of working end 64. Alternatively still, a portion of tool 60 may serve as a probe or testing device, such as a pressure gauge or electrical test screwdriver. Although only one tool 60 is shown in FIG. 1, a plurality of tools 60 may also be mounted on tooling end 50, each typically having a unique working end 64 in accordance with any embodiment described herein.

Figure 2A:
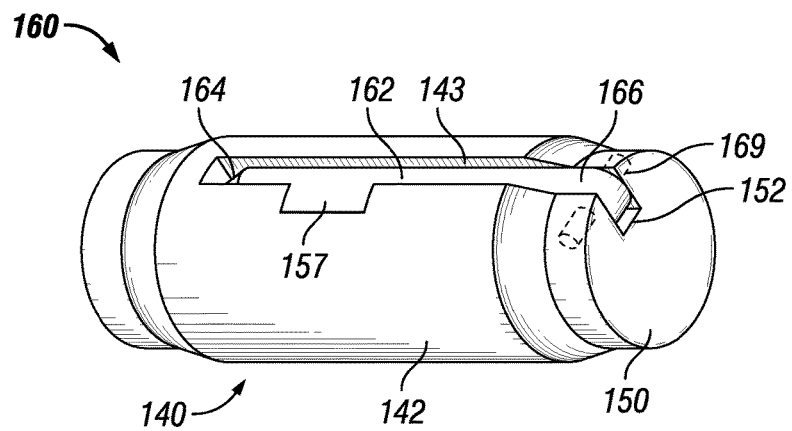
FIG. 2A is a perspective view of a handle body and tool according to another embodiment of the present disclosure, the tool being in a first position.
Figure 2B:
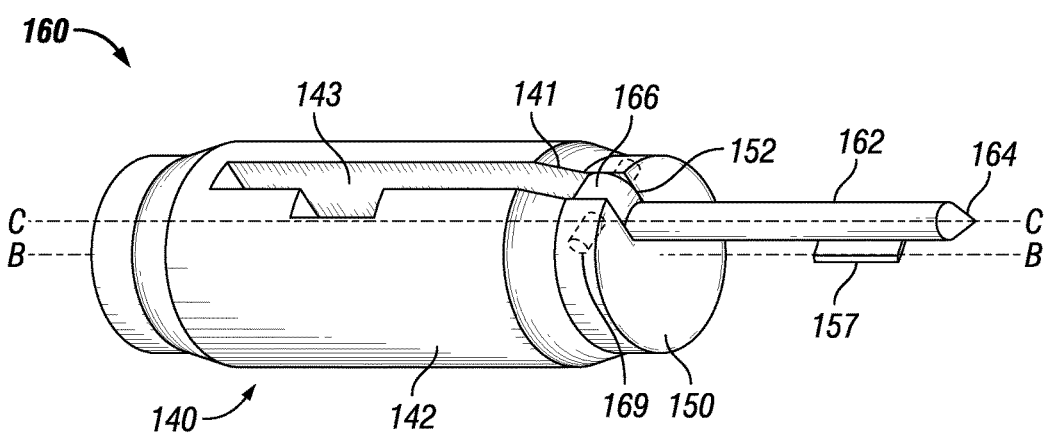
FIG. 2B is a perspective view of the handle body and tool of FIG. 2A, the tool being in a second position.

Any embodiment of at least one tool 60 may also be mounted to handle body 40 in a variety of ways. Tool 60 is depicted as being rigidly connected to handle body 40 in the embodiment of FIG. 1. For example, connection end 63 may be welded to tooling end 50 at connection point 52. Desirably, a rigid mount maximizes the amount of torque that can be applied by working end 64 and eliminates the risk of misplacing tool 60 independent of handle body 40. In some embodiments of tool 60, however, it may also be desirable to mount tool 60 on the handle body for movement between a stored position and a working position. A moveable embodiment of tool 60 is depicted in FIGS. 2A-2B as at least one tool 160. Preferably, tool 160 is stored within a handle body 140 in the stored position to avoid any possible interference with the tunneling procedures. For example, as shown in FIGS. 2A-B, an exterior surface 142 of a handle body 140 has a depression 143 that extends into handle body 140 so that the tool 160 can be stored in the depression. By storing tool 160 in depression 143, a surgeon is less likely to inadvertently disrupt the tunneling procedure by snagging working end 164 on another object in the operating room when moving handle body 140 and tunneling shaft 20, 120, or 220 to create a tunnel in the body.

In FIGS. 2A-B, connecting end 161 of tool 160 is rotatably mounted to tooling end 150 of the handle at a connection point 152 by a hinge 166 having a hinge pin 169 located adjacent to an exterior surface 142 of handle body 140 which defines an opening 141. A second actuator 157 may be used to move tool 160 in and out of depression 143. For example, second actuator 157 is depicted in FIGS. 2A-B as a tab 157 mounted on shaft 162 of tool 160. Thus, application of a moving force to second actuator or tab 157 rotates the tool 160 about hinge pin 169 into a stored position within depression 143, or from the stored position to the working position shown in FIG. 2B. A portion of depression 143 may be further offset around second actuator 157 to provide room for a finger to be slid thereunder. Preferably, the exterior surfaces of tool 160 and second actuator 157 are curved to fit flush with exterior surface 142 of handle body 140 when stored in depression 143. Advantageously, this allows the surgeon to grip handle body 140 as would normally be done without tool 160. The proximity of hinge 166 to exterior surface 142 and comparative size of handle body 140 relative to tool 160 also permits a plurality of tools 160 to be stored within a plurality of depressions 143 on handle body 140. For example, although not shown in FIGS. 2A-B, a second tool may be mounted adjacent to or opposite of first tool, such that either the first or second tool may be rotated into a stored position within a corresponding depression on handle body 140.

Figure 3A:
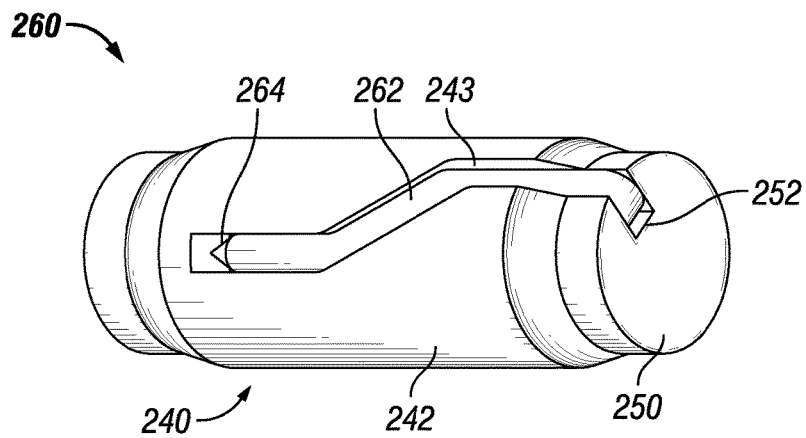
FIG. 3A is a perspective view of a handle body and tool according to a further embodiment of the present disclosure, the tool being in a first position.
Figure 3B:
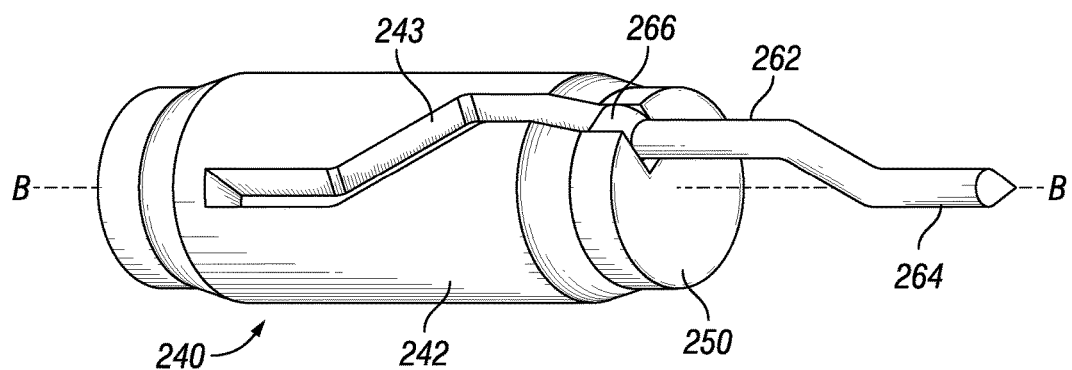
FIG. 3B is a perspective view of the handle body and tool of FIG. 3A, the tool being in a second position.

In FIG. 2B, shaft 162 of tool 160 extends out from handle body 140 along a tooling axis C-C that is offset from handle axis B-B but parallel to axis B-B. Desirably, this configuration simplifies the structure of tool 160 and depression 143. Certain embodiments of working end 164, such as a screwdriver, may function best if coaxial with handle axis B-B. Elements of combination tool 100 can be modified for this purpose. For example, as shown in FIGS. 3A-B, a tool shaft 262 is bent or curved relative to handle axis B-B to ensure that a working end 264 is coaxial with axis B-B, even if a hinge 266 remains proximate to exterior surface 242 of handle body 240. Tool shaft 262 extends into tooling end 250 at connection point 252 (FIG. 3A). The size, location and alignment of hinge 266 or depression 243 relative to handle body 240 may also be modified to store tool 264. For example, depression 243 may be curved to wrap around exterior surface 242 of handle body 240 about axis B-B. Advantageously, this allows handle body 240 to operate working end 264 without any off-axis eccentricities that may otherwise affect the amount of turns required to actuate an element of the implantable device.

Figure 4A:
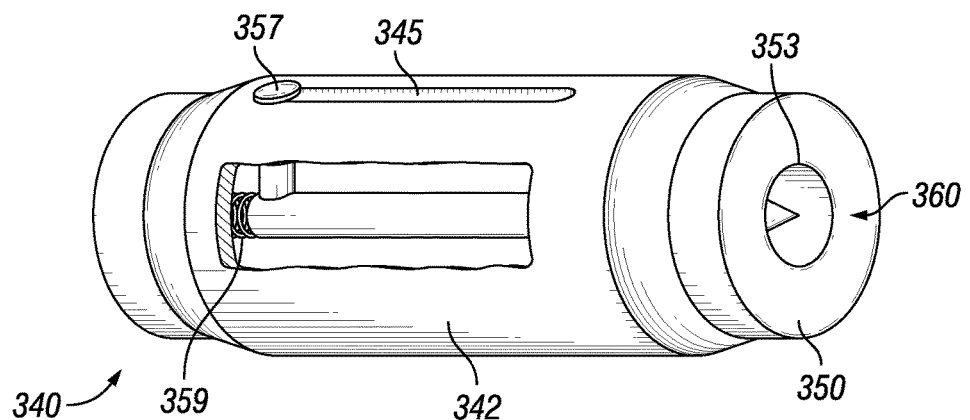
FIG. 4A is a partial cutaway perspective view of a handle body and tool according to yet another embodiment of the present disclosure, the tool being in a first position.
Figure 4B:
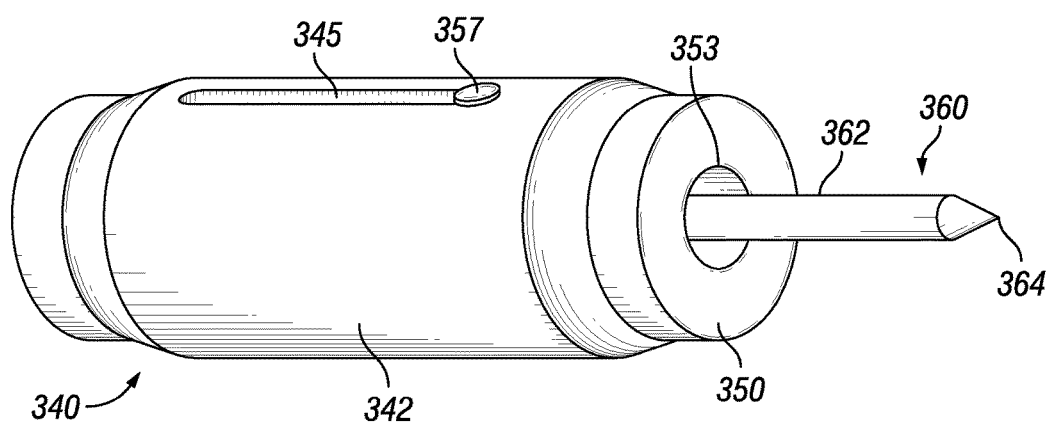
FIG. 4B is a perspective view of the handle body and tool of FIG. 4A, the tool being in a second position.

Other modes of moving tool 60 from a stored position to a working position, and vice versa, are also described in this application. In FIGS. 4A-B, for example, a tool receiving bore 353 extends into a handle body 340 from a tooling end 350. Similar to above, tool 360 is preferably at least partially contained within the tool receiving bore 353 in the stored position. A second actuator 357 is attached to tool 360.

Preferably, a portion of second actuator 357 extends out of a slot 345 that extends through exterior surface 342 of handle body 340 along an axis parallel to handle axis B-B. In this configuration, tool 360 is moved into either the working or stored positions by application of moving force to second actuator 357. For example, as shown in the cut-out section of FIG. 4A, second actuator 357 is preferably used to slide tool 360 out of bore 353 along handle axis B-B from the stored position depicted in FIG. 4A to the working position depicted in FIG. 4B showing the tool 360 having tool shaft 362 and working end 364. Although depicted as being coaxial with handle axis B-B, it should be appreciated that bore 353 may extend into handle body 340 at any point on tooling end 350. Thus, if the central portions of handle body 340 are occupied by the mechanism associated with first actuator 55, then bore 353 may be located proximate to exterior surface 342.

Figure 5A:
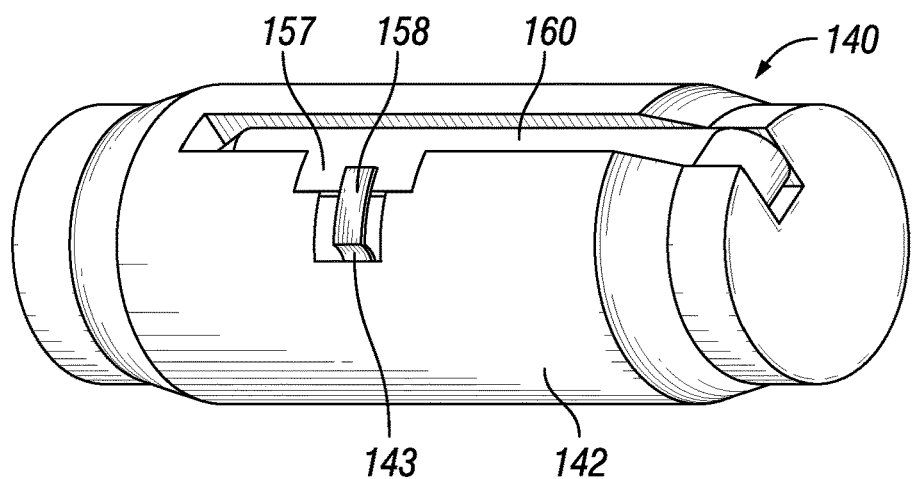
FIG. 5A is a perspective view of the handle body and tool of FIG. 2A including a control element according to an embodiment of the present disclosure.
Figure 5B:
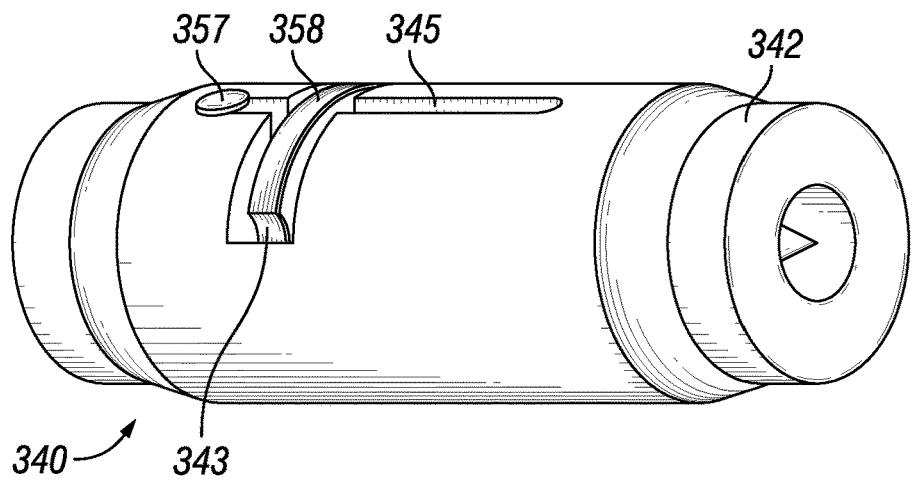
FIG. 5B is a perspective view of the handle body and tool of FIG. 4A including a control element according to another embodiment of the present disclosure.

It may be desirable to hold tool 160 in either the stored or working positions. Therefore, any moveable embodiment of tools 60 described above may be biased toward either the working or stored positions. Tool 160 may, for example, have flat bar or leaf-type spring (not shown) that biases tool 160 towards the open or closed position yet allows tool 160 to move into a different position if a pre-determined amount of force is applied to second actuator 157. As another example, tool 360 might be attached to a spring 359 (FIG. 4A) in tool receiving bore 353 that springs tool 560 into the working position upon activation of second actuator 357. It may also be desirable to lock tool 160, 260, or 360 in either the stored or working position. Thus, handle body 40 may be further adapted to have a control element. As shown in FIGS. 5A-B, either of handle body 140 or 340 may further comprise a control element 158 or 358 movable between a lock position, in which the control element 158 or 358 holds second actuator 157 or 357 in the stored position; and a release position, in which tool 160 or 360 is free to move toward the working position. In FIGS. 5A-B, for example, the control element is a slide lock 158 or 358 that is slidably mounted on exterior surface 142 or 342 of handle body 140 or 340 to be moveable within an extended portion of depression 143 or 343. Although not shown, control element 158 or 358 may alternatively be lever lock rotatably mounted on handle body 140 or 340, for example, to retain tool 160 or 360 in the stored position until rotated into an unlocked position. Desirably, control elements 148 and 348 may also serve as a safety lock that prevents tool 140 or 340 from moving out of the stored position until the safety lock is disengaged.

The number of specialized tools required to complete a procedure may exceed the storage capabilities of handle body 40. Therefore, it is further contemplated that an embodiment of tool 60 may be releasably mounted to a portion of handle body 40. As shown in FIGS. 6A-B, for example, a tool 460 has a connection end 463 with at least one detent mechanism 465. The exemplary embodiment of detent mechanism 465 depicted in FIG. 6B has a pair spring-loaded balls captured within a pair of holes in connection end 463. In complement, tooling end 450 of handle body 440 has a tool receiving opening 457 at connection point 452 that is adapted to receive connection end 463. Preferably, an interior surface of opening 457 has an indention 448 (FIG. 6B) engageable with detent mechanism 465 when connection 463 is received in tool receiving opening 457. By virtue of this configuration, tool 460 may be removably secured to handle body 440 by detent mechanism 465 and releasable by application of a removal force along handle axis B-B. Advantageously, this configuration minimizes the depth of tool receiving opening 457 along axis B-B to avoid the possibility of interference with the mechanisms associated with first actuator 55.

Figure 7A:
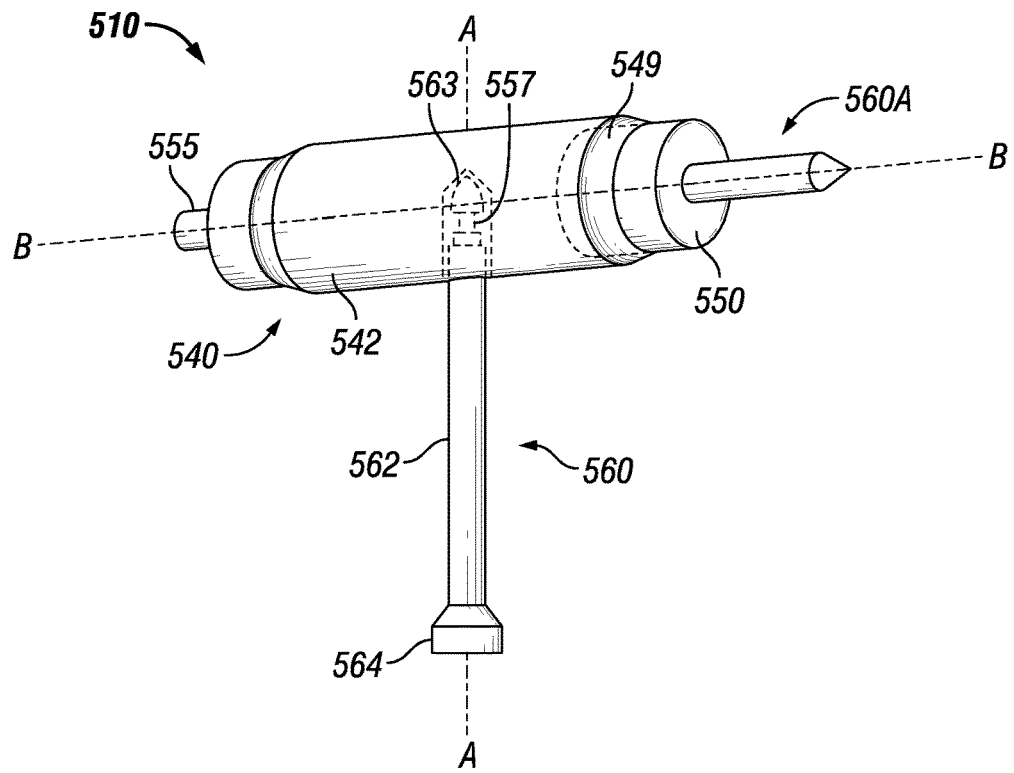
FIG. 7A is a perspective view of a handle body and tool according to still another embodiment of the present disclosure.
Figure 7B:
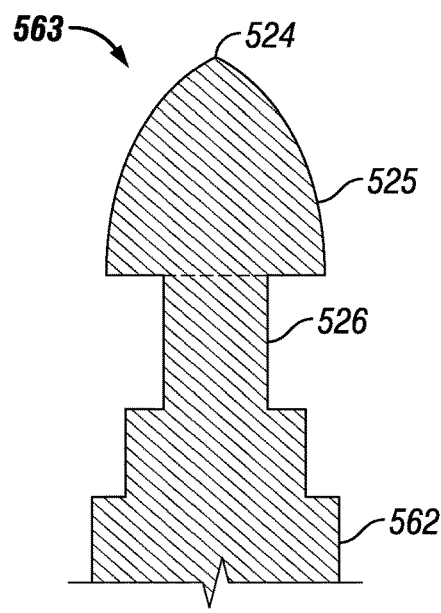
FIG. 7B is an enlarged, cross-sectional view of a connection end of the tool of FIG. 7A.

In still other embodiments, a tool 560 having exterior surface 542 may be releasably mounted to handle body 540 along an axis transverse to handle axis B-B, such as shaft axis A-A. An exemplary embodiment of a handle body 540 and tool 560 are depicted in FIGS. 7A-B. In this embodiment, the tool 560 is provided with a connection end 563 identical to the connection end 21 of the tunneling shaft discussed above with reference to FIG. 1, whereas the shaft opening 557 is similar to the shaft opening 41 of the handle discussed above with reference to FIG. 1. For example, FIG. 7B depicts the connection end 563 having a tip 524 defined by a tapered surface 525 and a groove 526. The handle also has an engagement rod (not shown) similar to the engagement rod 56 depicted in FIG. 1. Thus, the tool 560 can be installed in shaft opening 557 in place of a tunneling shaft. In this installed condition, the tool extends along axis A-A. The opening optionally may be provided with non-circular features (not shown) such as splines, teeth, or flat surfaces, and the body of tool 560 may be provided with mating features to prevent or limit rotation of the tool body with respect to the handle about axis A-A when the tool body is inserted in the opening. In a variant of this approach, the handle body may be provided with a separate opening (not shown) extending along another axis transverse to axis B-B.

The interchangeability of the tool and tunneling shaft offers several advantages. For example, if tooling end 550 of handle body 540 is rigidly connected to another tool, such as the exemplary screw driver 560A shown in FIG. 7A, then handle body 540 may still be utilized to operate a plurality of additional tools having a common connection end 563. Screw driver 560A may, for example, have a torque limiting element that occupies an end portion 549 of handle body 540 proximate to tooling end 550, thereby limiting the storage capacity of handle body 540. Because of the aforementioned interchangeability, handle body 540 may be rotated about handle axis B-B to operate screw driver 560A and moved relative to shaft axis A-A to operate releasable tool 560. As a further example, working end 564 of releasably mounted tool 560 may be a closed wrench with an elongated shaft 562 adapted to actuate a connecting element of an implantable device located in the thorax of the body, proximate to the heart. In this embodiment, the T-shaped grip provided by handle body 540 may be used to impart higher degrees of force to working end 564.

The varied embodiments of handle body 540 and tool 560 may also be adapted to actuate a mixture of local and remote connection components. For example, fixed tool 560A may be torque-limited to actuate a sensitive clamp adjacent the heart by applying a pre-determined amount of torque to an element of the clamp, whereas releasable tool 560 is one of a set of closed end wrenches, each typically having a unique working end 564 adapted to interconnect sub-elements of the implantable device. In the embodiment of FIG. 7A, first actuator 555 may be used to release either shaft 20 or tool 560 from handle body 540 without modification.

Each of the handles discussed herein desirably incorporates a shaft opening and first actuator for releasably engaging a tunneling tool as discussed above with reference to FIG. 1. The varied embodiments of handle body 40 described above also permit variations of first actuator 55. For example, in the embodiment of FIGS. 6A-6B, the first actuator at the actuator end of the tool body may be modified to release tool 460 from tooling receiving opening 457. As discussed above with reference to FIG. 1, depressing the first actuator 55 may cause rod 56 to move along handle axis B-B so as to disengage the tunneling shaft. The same motion can be used to disengage the connection end 463 of the tool from tool receiving opening 457 (FIG. 6A). For example, the disengagement element may be a portion of rod 56 that slides along an interior surface of handle body 440 to disengage detent mechanism 465 (FIG. 6B) from indention 448 in opening 447. Desirably, this allows the first actuator to release tool 460 and shaft 20 from handle body 440.

Any of the method steps disclosed herein may be modified to accommodate the structure of each alternative embodiment described above. For example, the preferred mounting step may further comprise the step of operating second actuator 157, 257 or 357 to move tool 160, 260 or 360 from a stored position to a working position. The exemplary method may also include the steps of mounting at least one tool 460 or 560 on handle body 440 or 540 prior to using working end 464 or 564. Methods of using tunneling shaft 120, for example, may include the step of attaching the implantable element to the at least one hole 128 prior to advancing the implantable element through the tunnel. Likewise, methods of using tunneling shaft 220 may include the step of inserting a guidewire through a bore 230 (FIG. 9) to guide tunneling shaft 220, or other medical device, to an internal connection point in the body.

Figure 10A:
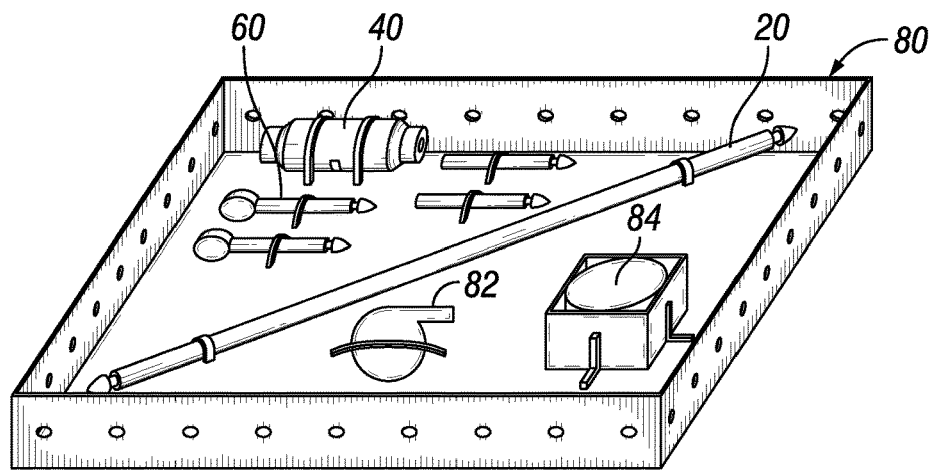
FIG. 10A is a schematic perspective view of a surgical kit including a container according to an embodiment of the present disclosure.

A further aspect of the present invention provides a kit of elements which can be used, for example, in installing an implantable medical device. One example of a surgical kit is depicted in FIG. 10A. The illustrated kit includes, for example, at least one tunneling shaft 20, a handle body 40, and at least one tool 60 in a container 80 that is sterilizable by known methods. A number of related components may also be stored in container 80. In FIG. 10A, for example, container 80 also has an exemplary hold-down 82 for securing one implantable device selected from a group consisting of a controller, a pump, a battery pack, an induction coil, a sensor, an element of a transcutaneous energy transfer system such as an induction coil, and any combination thereof. As shown, container 80 may also have a container 84 for holding any number of fixation elements associated with said implantable devices, such as a screw to be actuated by working end 64 of tool 60. Preferably, the contents of container 80 are secured therein to form a sterilizable assembly. Preferably still, the sterilizable assembly is autoclavable so that shaft 20, body 40, tool 60, and any other contents of container 80 may be delivered to the operating room in a sterilized condition.

The exemplary surgical kits described above may also be modified to accommodate the various embodiments of shaft 20, body 40, and tool 60 described herein. For example, an exemplary kit may include a plurality of tools 60, each tool 60 being permanently mounted on handle body 40 or adapted for temporary mounting on the handle body and having a working end 64 adapted to actuate an element of an implantable device. In other embodiments, an exemplary kit may include shaft 120 or 220 with a hole 128 or bore 230 as described above. Alternative kits may further comprise at least one elongated implantable element secured in the container, such as a guidewire, driveline, or like element. As noted above, numerous implantable devices may also be part of the kit.

Figure 10B:
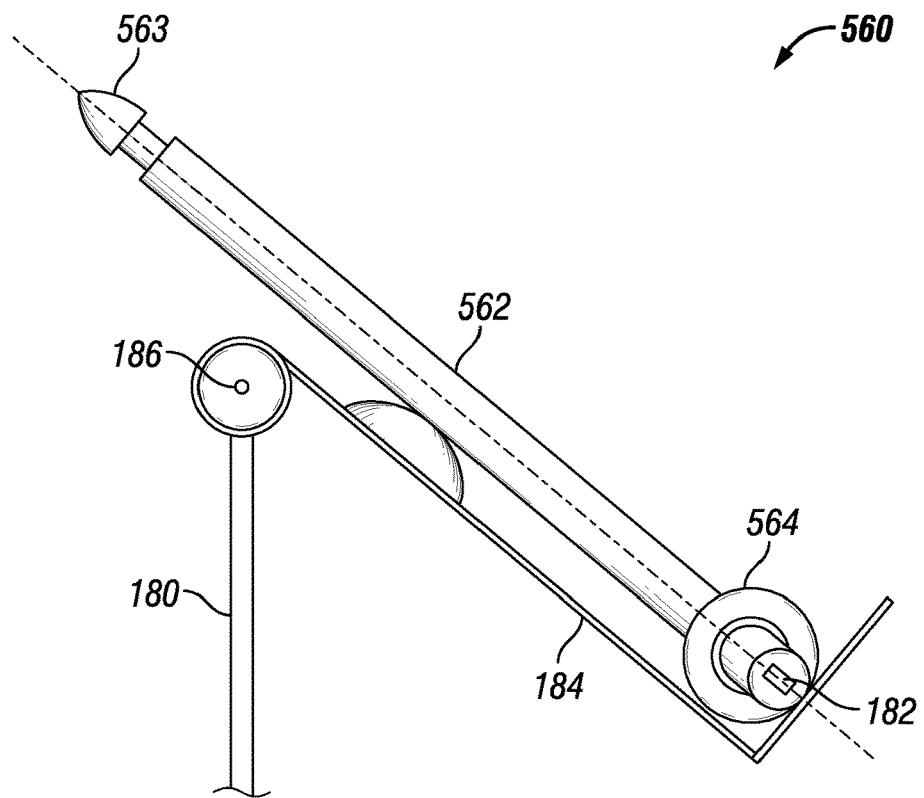
FIG. 10B is a schematic view of a container according to another embodiment of the present disclosure.

Alternative embodiments of container 80 are also contemplated as part of the present invention. As described above, for example, each tool 560 may have a connecting end 563 that is releasably mountable to a handle body 540. Preferably, as shown in FIG. 10B, a portion of tool 560 may also be mounted to a receiving portion 182 of a container 180. For example, working end 564 is an open wrench tool 560 that may be secured to receiving portion 182 of a platform 184 attached to a side wall of container 180. Preferably still, platform 184 is movable from a stored position, where each tool 560 is enclosed within container, to a working position, where connection end 563 of tool 560 is moved to an engageable position. In FIG. 10B, for example, platform 184 is pivotally mounted so that rotating platform 184 about a pivot 186 moves connection end 563 into an engageable position with respect to container 180.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical device comprising:
a handle body extending along a handle axis, the handle body being releasably engaged to a tunneling shaft extending along a shaft axis transverse to the handle axis; and
at least one tool mounted to the handle body, each said tool having a working end adapted to actuate an element of an implantable device, wherein the working end forms a wrench having a torque limiting element.

2. The device of claim 1, wherein the at least one tool is rigidly connected to the handle body.

3. The device of claim 1, wherein the at least one tool is mounted to the handle body for movement between a stored position and a working position, and wherein a portion of tool is contained within the handle body in the stored position.

4. The device of claim 3, further comprising an actuator operable to move the at least one tool from the stored position to the working position.

5. The device of claim 1, wherein the at least one tool is releasably mounted to the handle body.

6. The device of claim 5, wherein the at least one tool is releasably mounted to the handle body along an axis transverse to the handle axis.

7. The device of claim 6, wherein the handle body has an opening sized to receive a connecting end of the at least one tool and a connecting end of the tunneling shaft.

8. The device of claim 6 further comprising a release element, wherein operation of the release element releases either of the connecting end of the at least one tool or the connecting end of the tunneling shaft from the opening.

9. The device of claim 6, wherein the handle body has a first opening sized to receive a connecting end of the at least one tool and a second opening sized to receive a connecting end of the tunneling shaft, and wherein operation of an actuator releases either connecting end from the first or second opening.

10. The device of claim 1, wherein the tunneling shaft has at least one hole transverse to the shaft axis adjacent to the at least one tool.

11. A surgical device comprising:
a handle body extending along a handle axis, the handle body being releasably engaged to a tunneling shaft extending along a shaft axis transverse to the handle axis;
at least one tool mounted to the handle body, each said tool having a working end adapted to actuate an element of an implantable device, wherein the at least one tool is mounted to the handle body for movement between a stored position and a working position;
an actuator operable to move the at least one tool from the stored position to the working position; and
a depression in an external surface of the handle body that is shaped to receive the at least one tool in the stored position, wherein the actuator is a tab mounted on the at least one tool, wherein application of a force to the actuator rotates the at least one tool and the actuator about a point on the handle body to sit flush in the depression, and wherein a portion of the at least one tool is contained within the handle body in the stored position.

12. The device of claim 11, wherein the handle body has a tool receiving bore extending into the handle body, wherein the tool is at least partially contained within the tool receiving bore in the stored position, and wherein operation of the actuator slides the at least one tool out of the tool receiving bore.

13. A surgical device comprising:
a handle body extending along a handle axis, the handle body being releasably engaged to a tunneling shaft extending along a shaft axis transverse to the handle axis; and
at least one tool mounted to the handle body, each said tool having a working end adapted to actuate an element of an implantable device, wherein the at least one tool is mounted to the handle body for movement between a stored position and a working position, and wherein a portion of the at least one tool is contained within the handle body in the stored position;
an actuator operable to move the at least one tool from the stored position to the working position, wherein the actuator includes a spring element engaged between the at least one tool and the handle body to bias the at least one tool toward the working position; and
a control element movable between a lock position, in which the control element holds the actuator in the stored position, and a release position, in which the tool is free to move toward the working position.

14. The device of claim 13, further comprising a safety lock that prevents the tool from springing out of the stored position until the safety lock is disengaged.

15. A surgical device comprising:
a handle body extending along a handle axis, the handle body being releasably engaged to a tunneling shaft extending along a shaft axis transverse to the handle axis; and
at least one tool mounted to the handle body, each said tool having a working end adapted to actuate an element of an implantable device, wherein the at least one tool is mounted to the handle body for movement between a stored position and a working position, wherein the tunneling shaft has at least one hole transverse to the shaft axis adjacent to the at least one tool, and wherein the at least one hole on the tunneling shaft is in communication with a bore extending through the tunneling shaft and the handle body along the shaft axis.

16. A surgical kit comprising:
at least one tunneling shaft extending along a shaft axis;
a handle body extending along a handle axis, the handle body being engageable with each tunneling shaft so that the shaft axis is transverse to the handle axis;
a plurality of tools, each said tool being permanently mounted on the handle body or adapted for temporary mounting on the handle body, each said tool having a working end adapted to actuate an element of an implantable device;
a container including the at least one tunneling shaft, the handle body, and the plurality of tools being disposed within the container; and
at least one elongated implantable element secured in the container, the container, the handle body, the plurality of tools, and the at least one elongated implantable element stored in the container forming an autoclavable sterilizable assembly, and wherein the sterilizable assembly further comprises at least one implantable device selected from a group consisting of a controller, a pump, a battery pack, an induction coil, and a sensor.

17. The kit of claim 16, wherein each of the plurality of tools has a connecting end that is releasably mountable to the handle body, and wherein each connecting end may be releasably mounted to the handle body while the plurality of tools are stored in the container.

* * * * *